United States Patent [19]

Van Hale

[11] Patent Number: 5,531,722
[45] Date of Patent: Jul. 2, 1996

[54] ASPIRATION UNIT

[76] Inventor: Gregory L. Van Hale, 247 W. Glenoaks, Glendale, Calif. 91202

[21] Appl. No.: 343,038

[22] Filed: Nov. 21, 1994

[51] Int. Cl.⁶ .......................... A61M 25/00; A61B 17/20; A61C 17/06; A61C 1/16
[52] U.S. Cl. .............................. 604/280; 604/22; 433/92; 433/116
[58] Field of Search .............................. 128/763; 433/91, 433/92, 116, 119, 143, 96; 604/19, 22, 110, 113, 118, 119, 128, 263, 268, 313, 315, 902, 280, 284

[56] References Cited

U.S. PATENT DOCUMENTS

| | | | |
|---|---|---|---|
| 4,747,820 | 5/1988 | Hornlein et al. | 604/22 |
| 4,764,165 | 8/1988 | Reimels et al. | 604/22 X |
| 4,909,249 | 3/1990 | Akkas et al. | 604/22 X |
| 5,122,153 | 6/1992 | Harrel | 604/22 X |
| 5,181,916 | 1/1993 | Reynolds et al. | 604/22 X |
| 5,378,150 | 1/1995 | Harrel | 604/22 X |

*Primary Examiner*—John D. Yasko
*Assistant Examiner*—Adam J. Cermak
*Attorney, Agent, or Firm*—J. E. Brunton

[57] ABSTRACT

An aspiration unit that can be readily connected to an ultrasonic scaler of conventional design which includes a novel suction means for automatically carrying away from the work site cooling water and debris generated during the performance of the scaling procedure. The unit includes a transparent, tip-encompassing shroud that uniquely functions as a suction scoop for automatically capturing aerosols in the operative field including aerosols containing saliva, blood, tissue, calculus and like adherent deposits which are generated during the scaling procedure. The aspiration unit includes novel connectors that enable the unit to be removably connected to a conventional scaler so that the assemblage can be operated by the dentist using one hand without the aid of a dental assistant thereby decreasing the number of people exposed to any pathogens encountered during the scaling procedure.

18 Claims, 3 Drawing Sheets

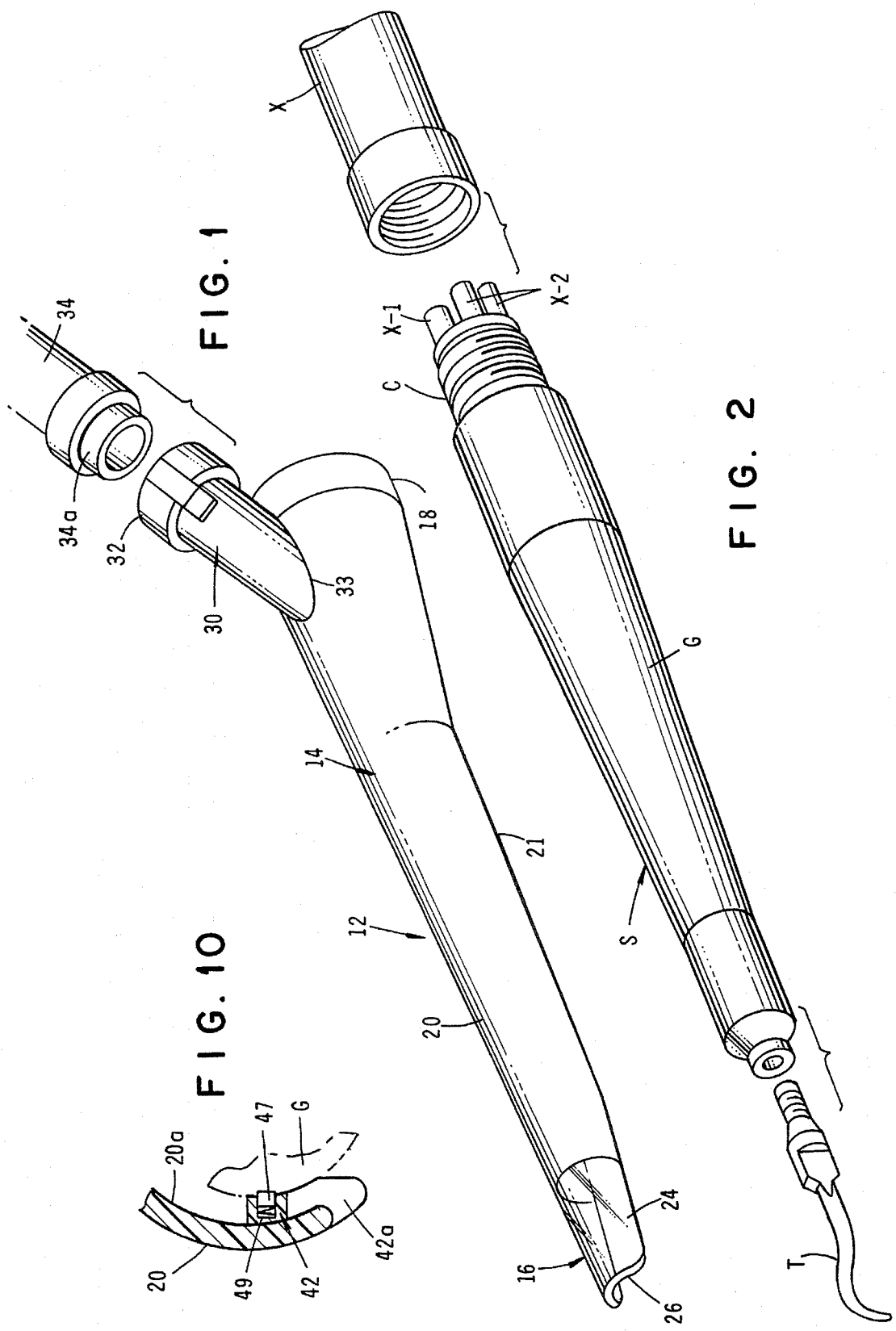

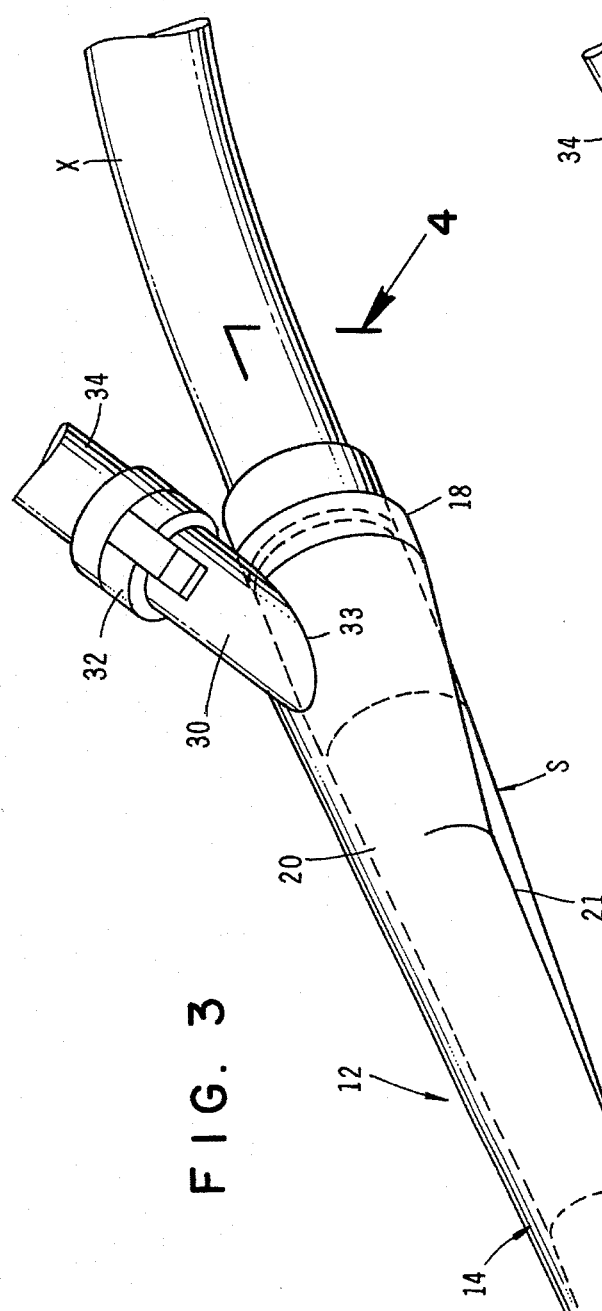
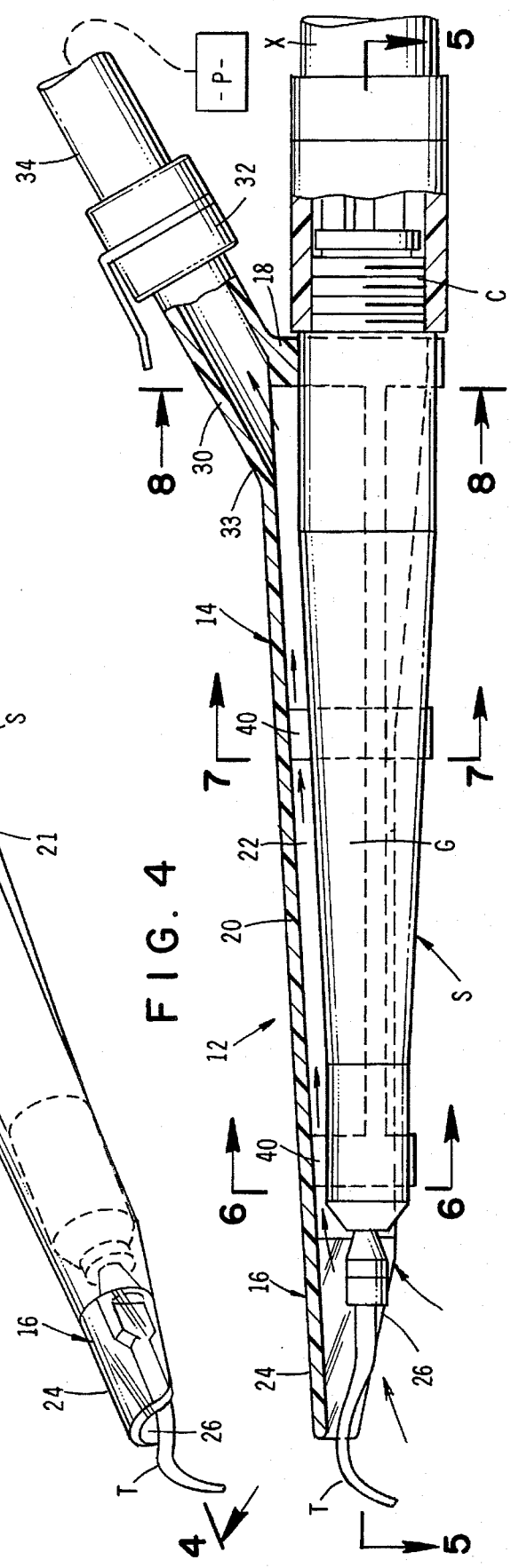
FIG. 3
FIG. 4

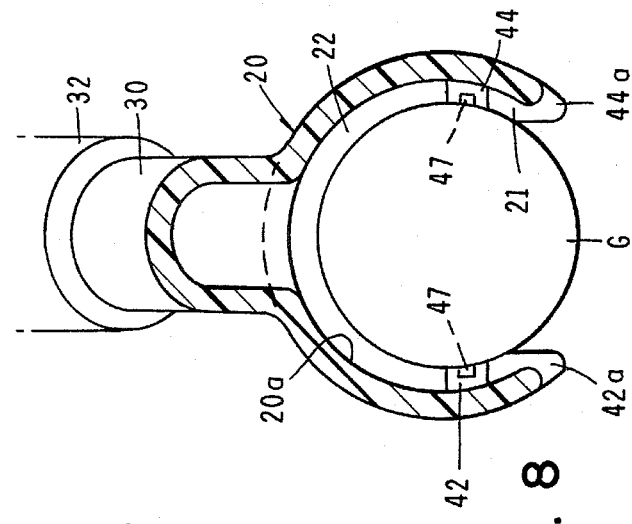
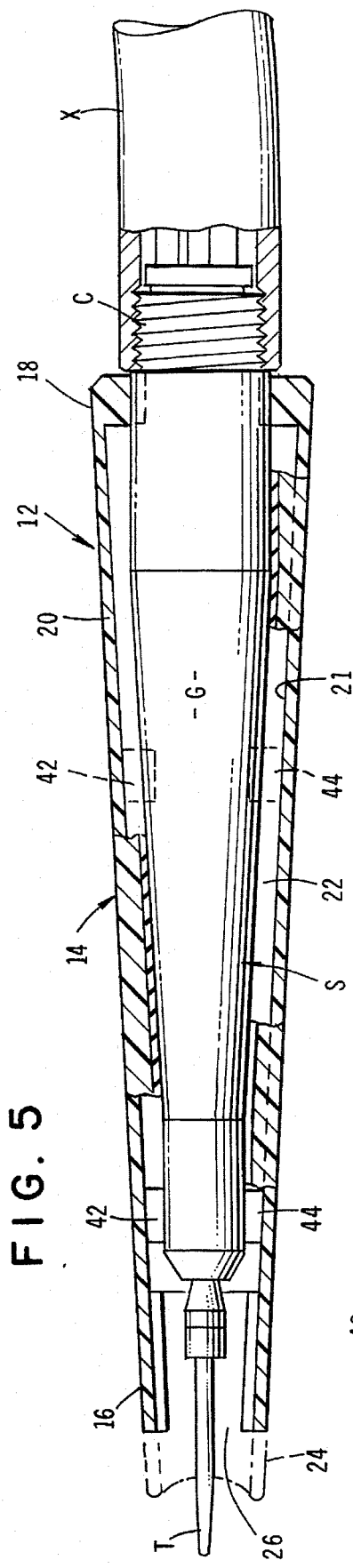
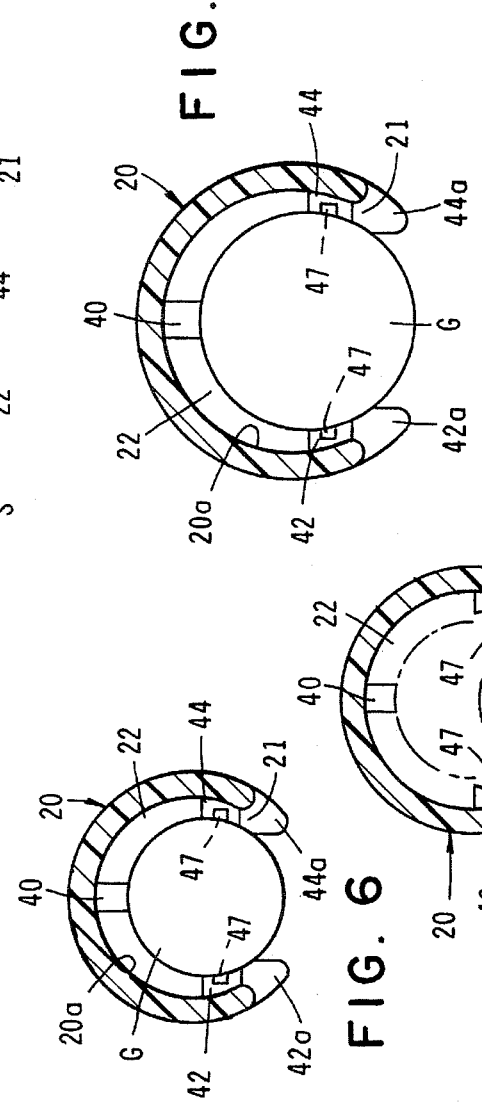
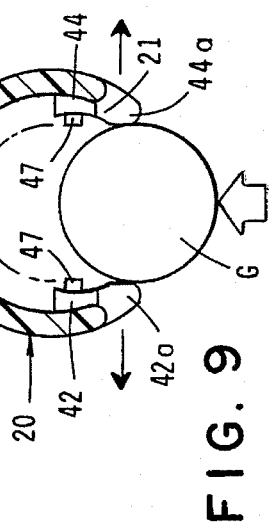

ASPIRATION UNIT

BACKGROUND OF THE INVENTION

1. Field of the Invention

The present invention relates generally to dental instruments. More particularly, the invention concerns a disposable aspirating unit usable with ultrasonic dental scalers of conventional construction. The aspirating unit has at its distal end a vacuum scoop that circumscribes the scaler tip and automatically carries away particulate matter generated during operation of the scaler.

2. Discussion of the Invention

A number of different types of ultrasonic scalers have been suggested in the past. Typically such devices include a curved tip for supplying high frequency vibrations that effectively remove adherent deposits from the teeth and bits of inflamed tissue from the walls of the gingival crevice. Most of the prior ultrasonic scalers include an autoclavable hand piece and one or more tips that can be removably connected to the hand piece. The tip of the scaler is generally interconnected with an electrically operated power unit which provides high frequency vibration to the tip in the range of between about 5,000 Hertz and about 25,000 Hertz. Exemplary of such ultrasonic scalers are those offered for sale by Dentsply International, Inc. of York, Pa.; J. R. Rand Corporation of Deer Park, N.Y.; and Spartan U.S.A. of Fenton, Mo.

During operation of the conventional prior art ultrasonic scalers, substantial aerosol contamination results. More particularly, during the scaling procedure, the prior art devices typically generate a substantial aerosol spray of blood, saliva, tissue, calculus and other particulate matter which can contaminate large areas of the operative field.

Some prior art ultrasonic scalers are provided with a source of cooling water which can be directed toward the work area. These devices tend to cause a build-up of water in the patient's mouth which must be periodically removed using conventional suction devices. Generally these devices include an elongated tube having a suction nozzle at one end which is disposed within the patient's mouth proximate the tooth being worked on. These suction devices are generally unwieldy and must be operated by the dental assistant as the dentist performs the scaling procedure. Accordingly, two people, that is the dentist and the dental assistant, both must be present during the dental procedure.

The thrust of the present invention is to overcome the drawbacks set forth in the preceding paragraphs by providing a novel, disposable aspiration unit that can be quickly and easily removably interconnected with commercially available scalers of conventional design. The aspiration unit of the present invention is lightweight, easy to use and provides novel suction means for automatically carrying away both the cooling water used during the procedure and the particulate contamination generated during the performance of the procedure. Since the dentist is manipulating the scaler along with the attached aspiration unit of the invention, the dental assistant is not needed and can be performing other important work such as sterilization in accordance with recent OSHA procedures.

While some attempts have been made in the past to provide suction devices for use with ultrasonic scalers, these devices have not received wide acceptance in the field. One prior art suction device which has been advertised for use with ultrasonic scalers is a device offered for sale by Periogiene Company of Fort Collins, Colo.

As will be better understood from the description which follows, the disposable aspiration unit of the present invention provides high volume aspiration and, due to its unique design, effectively contains and carries away aerosols containing blood, tissue and particulate matter generated during the scaling procedure.

SUMMARY OF THE INVENTION

It is an object of the present invention to provide an aspiration unit that can be readily connected to an ultrasonic scaler of conventional design which includes a novel suction means for automatically carrying away from the work site cooling water and debris generated during the performance of the scaling procedure.

More particularly, it is an object of the invention to provide an aspiration unit of the aforementioned character which includes a tip-encompassing shroud that uniquely functions as a suction scoop for automatically capturing aerosols in the operative field including aerosols containing saliva, blood, tissue, calculus and like adherent deposits which are generated during the scaling procedure.

Another object of the invention is to provide an aspiration unit including a novel suction system that can be connected to a conventional scaler so that the assemblage can be operated by the dentist or dental hygenist using one hand without the aid of a dental assistant thereby decreasing the number of people exposed to any pathogens encountered during the scaling procedure.

Another object of the invention is to provide an aspiration unit of the class described that is compatible with standard sources of vacuum typically found in dental facilities.

Another object of the invention is to provide an apparatus as described which dramatically decreases the amount of airborne particles, aerosols and other contaminates which may be generated during the scaling procedure.

Another object of the invention is to provide an aerosol unit of the character described in the preceding paragraph which is of simple design for ease of manufacture and one which can be inexpensively produced in large volume.

Still another object of the invention is to provide an aspiration unit having a lightweight, plastic body portion which is disposable and can be removably attached proximate one end to a source of vacuum and is provided proximate its other with a suction scoop of novel design which efficiently captures the cooling water and the debris generated during the scaling operation.

BRIEF DESCRIPTION OF THE DRAWINGS

FIG. 1 is a generally perspective view of one form of aspiration unit of the invention.

FIG. 2 is a generally perspective view of a scaler of conventional construction of the character with which the aspiration unit can be used.

FIG. 3 is a generally perspective view showing the aspiration unit of the invention interconnected with the conventional scaler unit.

FIG. 4 is a cross-sectional view taken along lines 4—4 of FIG. 3.

FIG. 5 is a cross-sectional view taken along lines 5—5 of FIG. 4.

FIG. 6 is a cross-sectional view taken along lines 6—6 of FIG. 4.

FIG. 7 is a cross-sectional view taken along lines 7—7 of FIG. 4.

FIG. 8 is a cross-sectional view taken along lines 8—8 of FIG. 4.

FIG. 9 is a generally diagrammatic, cross-sectional view illustrating the manner of interconnection of the aspiration unit of the invention with the conventional scaler unit.

FIG. 10 is an enlarged, fragmentary view similar to FIG. 7 but showing the construction of the spring-loaded detend of the gripping elements.

DESCRIPTION OF THE INVENTION

Referring to the drawings and particularly to FIGS. 1 through 4, one form of the aspiration unit of the present invention is there shown and generally designated by the numeral 12. The unit comprises an elongated, specifically configured plastic body 14 having first distal and second proximal end portions 16 and 18 respectively. Body 14 includes an outer wall which is generally "C" shaped in cross section and includes a longitudinally extending bottom opening 21. Wall 20 progressively increases in diameter from the first end portion 16 to the second end portion 18 (FIGS. 6 through 8). Provided proximate the first or distal end portion 16 of body 14 is an intake means shown here as a specially configured, transparent shroud, or scoop-like portion 24 having an open mouth 26. Being transparent, portion 24 in no way obstructs the vision of the tip during the scaling procedure.

An important feature of the present invention is the uniquely configured, longitudinally extending interior space 22 which is defined by wall 20 of body 14. Space 22 communicates with a vacuum means which here includes a vacuum pump "P" of standard construction (FIG. 4). Vacuum pump "P" is uniquely interconnected with interior space 22 by an angularly upwardly extending tubular conduit 30 having an outer end portion 32. The inner end 33 of conduit 30 is integrally formed with body 14 intermediate ends 16 and 18 (FIG. 4). As best seen in FIG. 1, the end portion 34a of a vacuum supply line 34 is adapted to be telescopically received within tubular end portion 32 of conduit 30. In a manner presently to be described, vacuum pump "P" communicates with supply line 34 so as to create a substantial vacuum within interior space 22 that is sufficient to capture and channel through space 22 both the accumulated cooling water and the particulate contamination located proximate scaler tip "T". It is to be understood that any source of vacuum, including in-office high and low pressure sources of vacuum, can be used in lieu of a vacuum pump. For example, through proper design of end portion 32, low pressure saliva ejection systems typically found in dental offices can be used as the vacuum source.

The aspiration unit is detachably interconnected with the ultrasonic scaler "S" (FIG. 2) by novel connector means, the details of which will presently be described. As previously mentioned, scalers of the type shown in FIG. 2 are commercially available from various sources and typically include a hand grip portion "G", which terminates at one end in a connector portion "C" that enables the scaler to be connected to the power unit and to a source of cooling water (not shown) via a conduit "X". More particularly, a power cable X-1 connects tip "C" with the power source while water conduits X-2 provide cooling water to the end of tip "T". Provided at the other end of the scaler is means for interconnection of a selected tip "T".

Forming a very important aspect of the invention is the previously mentioned connector means for releasably interconnecting body 14 with a conventional, commercially available ultrasonic scaler. As best seen by referring to FIGS. 4 through 9, the connector means of the present invention comprise a plurality of longitudinally spaced gripping means for releasably gripping the hand grip portion of the ultrasonic scaler. The gripping means here comprise three sets of longitudinally spaced gripping elements which are connected to the inner surface of wall 20 and which extend radially inwardly into interior space 22. Each set of gripping elements comprises an upper, centrally located element 40 and two circumferentially spaced, oppositely disposed gripping elements 42 and 44 respectively. Each of the gripping elements 42 and 44 include a yieldably deformable terminal portion designated in the drawings as 42a and 44a respectively. Referring particularly to FIG. 9, which is exemplary of the operation of elements 42 and 44, it is to be noted that as the grip portion "G" of the scaler is introduced into longitudinally extending opening 21 provided in wall 20, elements 42 and 44 will yieldably deform in a manner to permit passage therebetween of grip portion "G" of the scaler. After the grip portion passes past terminal portions 42a and 44a they will automatically spring back to their normal expanded position shown in FIG. 6 wherein they securely grip the hand grip portion of the scaler in a manner to positively secure it within a portion of interior space 22. As is indicated in FIGS. 6 and 7, centrally disposed elements 40 function to engage the upper portion of the grip of the scaler so as to maintain the grip portion of the scaler centered within interior space 22.

It can also be observed from a study of FIGS. 6 through 10 that each of the gripping elements 42 and 44 is provided with a detent mechanism 47 which is movable against the urging of a biasing spring 49 (FIG. 10) from an extended position shown in FIG. 10 to a recessed grip-engaging position shown in FIGS. 6, 7, and 8. Detents 47 are of a conventional construction well known to those skilled in the art and the details of their construction need not be described herein. As indicated in FIGS. 6, 7, and 8, detents 47 along with terminal portions 42a and 44a of the gripping elements function to grippably engage the scaler so as to securely retain it within interior space 22 of the aspiration unit body.

With the ultrasonic scaler secured in position within body 14, it is to be noted that the portion of interior space 22 located between the inner surface 20a of wall 20 and the outer surface of the hand grip portion of the scaler is such as to provide a passageway of substantial volume. As indicated in FIG. 4, this passageway is in communication with mouth portion 26 of transparent shroud 24 so that, when a vacuum is formed within interior space 22 by the vacuum pump, air will be drawn rapidly into the mouth of the shroud 24 in the manner shown by the arrows in FIG. 4. The air will then pass around and about gripping elements 42 and 44 and will flow smoothly through the passageway in the manner indicated by the flow arrow of FIG. 4. This inward flow of air into mouth 26 and through internal space 22 will efficiently draw into the interior space 22 cooling water as well as particulate contamination generated by the tip "T" during the operation of the scaler device.

Another unique feature of the apparatus of the present invention resides in the angularly disposed conduit 30 which is integrally formed with body 14 and which is removably interconnected with supply line 44 in the manner indicated in FIGS. 3 and 4. More particularly, when portion 34a of the supply line is telescopically received within end portion 32 of conduit 30, a substantially leak-tight seal will result enabling a substantial vacuum to be exerted on internal space 22 upon activating vacuum pump "P". As previously mentioned, this vacuum is more than sufficient to cause a substantial inflow of air through mouth 26 of shroud 24 causing both cooling water and particulate matter located in the area of tip "T" to rapidly flow inwardly of the unit and through interior space 22 through conduit 30 and toward vacuum pump "P". In actual operation, the contaminated particulate matter is separated from the cooling water and appropriately disposed of by traditional filtering means of a character well known in the art (not shown).

After the scaling procedure has been completed, supply line 34 is disconnected from conduit 30 and body 14 is separated from the ultrasonic scaler by exerting a force on the body sufficient to deform gripping element 42a and 44a in the manner shown in FIG. 9. Once body 14 is free from the grip portion of the scaler, it can be conveniently disposed of in an appropriate safe receptacle along with other contaminated waste generated in the dental office.

At the commencement of the next scaling procedure, a new aspiration unit can be conveniently fitted over the sterilized scaler device and can be reconnected with supply line 34 and with connector conduit X in the manner indicated in FIGS. 1, 3, and 4.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. An aspiration unit usable in connection with a dental instrument having a hand grip portion and a tooth-engaging portion, said aspiration unit comprising:
   (a) an elongated body having a distal end, a proximal end and a wall defining an elongated interior space, said wall being generally semi-circular in cross section;
   (b) connector means for operably interconnecting said body with the dental instrument so that said wall of said body at least partially circumscribes the hand grip portion of the dental instrument;
   (c) intake means connected to said body proximate said distal end thereof in communication with said interior space of said body and at least partially circumscribing the tooth engaging portion of the dental instrument when said body is connected to the dental instrument for capturing particulate matter located proximate the tooth engaging portion of the dental instrument and for channeling said particulate matter into said interior space; and
   (d) vacuum means connected to said body proximate said proximal end thereof for creating a vacuum at said intake means.

2. An aspiration unit as defined in claim 1 in which said intake means includes a curved, substantially transparent shroud connected to said distal end portion of said body and partially circumscribing the tooth engaging portion of the dental instrument.

3. An aspiration unit as defined in claim 1 in which said connector means comprises a plurality of longitudinally spaced, yieldably deformable connector elements connected to said wall of said body and extending radially inwardly into said interior space for releasable engagement with the grip portion of the dental instrument.

4. An aspiration unit as defined in claim 1 in which the dental instrument further includes cooling water means for cooling an area proximate the tooth engaging portion of the instrument and in which said intake means is adapted to capture both cooling water and particulate matter located proximate the tooth engaging portion of the dental instrument.

5. An aspiration unit as defined in claim 1 in which said vacuum means comprises a tubular conduit connected to said body intermediate said distal and proximate ends, said tubular conduit being in communication with said interior space.

6. An aspiration unit as defined in claim 5 in which said tubular conduit extends angularly outward from said body.

7. An aspiration unit usable in connection with an ultrasonic scaler which includes a hand grip portion and a tip portion, said aspiration unit comprising:
   (a) an elongated body having a distal end, a proximal end and a wall defining an interior space, said wall having a longitudinally extending bottom opening for closely receiving the hand grip portion of the ultrasonic scaler;
   (b) connector means provided on said wall for releasably interconnecting said body to the hand grip portion of the ultrasonic scaler, said connector means comprising a plurality of longitudinally spaced gripping means for releasably gripping the hand grip portion;
   (c) intake means, including a transparent scoop-like shroud connected to said body proximate said distal end thereof, said shroud communicating with said interior space of said elongated body for capturing particulate matter generated by the tip portion of the ultrasonic scaler; and
   (d) vacuum means connected to said body for creating a vacuum at said intake means.

8. An aspiration unit as defined in claim 7 in which said wall of said body is generally "C" shaped in cross section.

9. An aspiration unit as defined in claim 7 in which said vacuum means includes a tubular conduit which is connected to said body intermediate said distal end and said proximal end and which extends angularly outward from said body.

10. An aspiration unit as defined in claim 7 in which said intake means includes a curved, substantially transparent shroud which partially circumscribing the tip portion of the ultrasonic scaler.

11. An aspiration unit as defined in claim 7 in which said gripping means comprises a plurality of longitudinally spaced, yieldably deformable connector elements connected to said wall of said body and extending radially inwardly therefrom into said interior space for releasably engaging with the grip portion of the ultrasonic scaler.

12. An aspiration unit as defined in claim 11 in which said connector elements include circumferentially spaced detents.

13. An aspiration unit as defined in claim 12 in which said connector elements include terminal portions extending downwardly from said wall of said body of said bottom opening.

14. An aspiration unit usable in connection with an ultrasonic scaler which includes a hand grip portion and a tip portion, said aspiration unit comprising:
   (a) an elongated body having a distal end, a proximal end and a wall defining an interior space, said wall being generally "C" shaped in cross section and having a longitudinally extending bottom opening for closely receiving the hand grip portion of the ultrasonic scaler;
   (b) connector means provided on said wall for releasably interconnecting said body to the hand grip portion of the ultrasonic scaler, said connector means comprising a plurality of longitudinally spaced gripping elements adapted to releasably grip the hand grip portion of the ultrasonic scaler, said gripping elements including yieldably deformable terminal portions extending downwardly from said wall of said body proximate of said bottom opening;

(c) intake means, including a transparent scoop-like shroud connected to said body proximate said distal end thereof, said shroud communicating with said interior space of said elongated body for capturing particulate matter generated by the tip portion of the ultrasonic scaler; and (d) vacuum means connected to said body for creating a vacuum at said intake means, said vacuum means including a tubular conduit which is connected to said body intermediate said distal end and said proximal end and which extends angularly outward from said body.

15. An aspiration unit as defined in claim 14 in which said gripping elements include detents for engagement with the hand grip portion of the ultrasonic scaler.

16. An aspiration unit as defined in claim 14 which said body and said tubular conduit are integrally formed from a moldable plastic.

17. An aspiration unit as defined in claim 16 in which said vacuum means includes:

(a) supply line having first and second ends, said first end being releasably connected to said tubular conduit; and (b) a vacuum pump connected to said second end of said supply line.

18. An aspiration unit as defined in claim 17 in which said tubular conduit includes an end portion adapted to telescopically receive said first end of said supply line.

* * * * *